(12) United States Patent
Ichinose et al.

(10) Patent No.: US 9,804,245 B2
(45) Date of Patent: Oct. 31, 2017

(54) MAGNETIC RESONANCE IMAGING APPARATUS AND MAGNETIC RESONANCE IMAGING METHOD

(75) Inventors: Nobuyasu Ichinose, Otawara (JP); Yuichi Yamashita, Nagareyama (JP)

(73) Assignee: TOSHIBA MEDICAL SYSTEMS CORPORATION, Otawara-shi, Tochigi-ken (JP)

( * ) Notice: Subject to any disclaimer, the term of this patent is extended or adjusted under 35 U.S.C. 154(b) by 1126 days.

(21) Appl. No.: 12/213,939

(22) Filed: Jun. 26, 2008

(65) Prior Publication Data

US 2009/0005670 A1 Jan. 1, 2009

(30) Foreign Application Priority Data

Jun. 29, 2007 (JP) .................. 2007-173204

(51) Int. Cl.
*A61B 5/05* (2006.01)
*G01R 33/563* (2006.01)
(Continued)

(52) U.S. Cl.
CPC ............ *G01R 33/5635* (2013.01); *A61B 5/05* (2013.01); *A61B 5/055* (2013.01); *G01R 33/20* (2013.01); *G01R 33/48* (2013.01); *G01R 33/4833* (2013.01); *G01R 33/4835* (2013.01); *G01R 33/4838* (2013.01); *G01R 33/543* (2013.01); *G01R 33/56308* (2013.01);
(Continued)

(58) Field of Classification Search
CPC .......... G01R 33/5607; G01R 33/56308; G01R 33/5635; G01R 33/56366
See application file for complete search history.

(56) References Cited

U.S. PATENT DOCUMENTS

| 4,797,615 | A | * | 1/1989 | Rotem et al. ................. 324/309 |
| 5,304,929 | A | * | 4/1994 | Fang et al. .................... 324/309 |

(Continued)

FOREIGN PATENT DOCUMENTS

| CN | 1147639 A | 4/1997 |
| CN | 1845702 A | 10/2006 |

(Continued)

OTHER PUBLICATIONS

Schmitt et al, T-One Insensitive Steady State Imaging (TOSSI): Obtaining TrueFISP images with pure T2 contrast, Proc. Intl. Soc. Mag. Reson. Med. 11 (2003).*

(Continued)

*Primary Examiner* — James Kish
(74) *Attorney, Agent, or Firm* — Nixon & Vanderhye P.C.

(57) ABSTRACT

An IR pulse is applied to a tag region B that is disposed at the upstream side of the ascending aorta relative to a tag region A at a timing with a second predetermined delay time TD2 (for example, 600 ms) from the application time of an IR pulse to the tag region A to thereby perform tagging. By this tagging, it is possible to suppress the MR signals derived from the substantial portions and the blood within the tag region B. Subsequently, an imaging scan is performed after a predetermined time lapse TIA (for example, 1200 ms) from the application time of the IR pulse to the tag region A or after a predetermined time lapse TIB (for example, 600 ms) from the application time of the IR pulse to the tag region B.

14 Claims, 15 Drawing Sheets

(51) Int. Cl.
    *A61B 5/055*    (2006.01)
    *G01R 33/20*    (2006.01)
    *G01R 33/54*    (2006.01)
    *G01R 33/48*    (2006.01)
    G01R 33/483   (2006.01)
    G01R 33/56    (2006.01)

(52) U.S. Cl.
    CPC ...... *G01R 33/56366* (2013.01); *G01R 33/483* (2013.01); *G01R 33/5607* (2013.01)

(56) References Cited

U.S. PATENT DOCUMENTS

| | | | |
|---|---|---|---|
| 5,751,145 A | 5/1998 | Shimizu | |
| 2008/0061780 A1* | 3/2008 | Yamada | A61B 5/0263 324/309 |
| 2008/0136411 A1 | 6/2008 | Miyoshi | |

FOREIGN PATENT DOCUMENTS

| | | | |
|---|---|---|---|
| CN | 101034153 A | 9/2007 | |
| CN | 101259018 A | 9/2008 | |
| EP | 1767957 A1 * | 3/2007 | ........... G01R 33/563 |
| JP | 5-91988 | 4/1993 | |
| JP | 5-309078 | 11/1993 | |
| JP | 2004-261619 | 9/2004 | |
| JP | 2005-296627 | 10/2005 | |
| JP | 2007-029763 | 2/2007 | |
| JP | 2008-67857 | 3/2008 | |

OTHER PUBLICATIONS

Bolar et al, Qantification of Regional Pulmonary Blood Flow Using ASL-FAIRER, Magnetic Resonance in Medicine, 55:1308-1317 (2006).*

Official Action dated Mar. 1, 2010 in CN200810128996.9 with English translation.

Nishimura et al., "Considerations of Magnetic Resonance Angiography by Selective Inversion Recovery", *Magnetic Resonance in Medicine*, vol. 7, 1988, pp. 472-484.

Office Action mailed Nov. 27, 2013 in CN201210021447.8 and English translation.

Japanese Office Action mailed on Jul. 16, 2013 in JP 2008-167593 with English translation.

Samuel J. Wang, et al., "Fast Angiography Using Selective Inversion Recovery," Magnetic Resonance in Medicine, 1992, vol. 23, Issue 1, p. 109-121.

* cited by examiner

MAGNETIC RESONANCE IMAGING APPARATUS AND MAGNETIC RESONANCE IMAGING METHOD

CROSS-REFERENCE TO RELATED APPLICATIONS

This application is based upon and claims the benefit of priority from prior Japanese Patent Application No. 2007-173204, filed Jun. 29, 2007, the entire contents of which are incorporated herein by reference.

BACKGROUND OF THE INVENTION

1. Field of the Invention

The present invention relates to a magnetic resonance imaging apparatus and a magnetic resonance imaging method suited to an observation of the dynamic state of a moving material in a body such as blood or cerebrospinal fluid (CSF).

2. Description of the Related Art

A magnetic resonance imaging apparatus is an apparatus that excites nuclear spins of atoms in a subject magnetically with a radio-frequency signal having the Larmor frequency and acquires an MR signal generated due to the excitation, thereby reconstructing an MRI image or an MRA image (hereinafter, collectively referred to as an MR image).

In recent years, in the art of the magnetic resonance imaging apparatus, a method is known in which inversion recovery (IR) pulses are applied to thereby perform labeling (tagging) on an observation target in the form of longitudinal magnetization in both time and space domains, and MR images are taken after a given time (for example, see "Considerations of Magnetic Resonance Angiography by Selective Inversion Recovery," D. G. Nishimura et al., Magnetic Resonance in Medicine, Vol. 7, pp. 472-484, 1988). By observing the images obtained by this method, it is possible to visually recognize the distribution of labeled observation target.

Another method is known which conducts labeling with longitudinal magnetization by a selective excitation method before echo signal collection for imaging, and takes a plurality of images while varying a time lapse TI from the labeling to the start of the imaging (for example, see Japanese Laid-open (Kokai) Patent Publication No. 2001-252263). The plural images obtained by this method are sequentially displayed at regular intervals, and therefore, it is possible to observe the dynamic state of a moving material in a body such as blood or cerebrospinal fluid.

Depending on portions of the body, however, blood may flow into the portion from multiple directions. When such a portion is included in an imaging region, it is difficult from the conventional method to label only the blood vessel that is to be diagnosed. Moreover, the velocity of blood flowing into the image region differs from blood vessel to blood vessel through which the blood flows. For this reason, the time lapse from the labeling to the start of the imaging is not appropriately set, with the result that a blood vessel that is not intended to be diagnosed is also imaged, making it difficult to observe the blood vessel that is to be diagnosed.

BRIEF SUMMARY

The present exemplary embodiment has been made in view of the above-described circumstances, and an object of the present invention is, therefore, to provide a magnetic resonance imaging apparatus and a magnetic resonance imaging method capable of appropriately labeling and visualizing only the blood vessel that is to be diagnosed.

According to an aspect of the present invention, there is provided that a magnetic resonance imaging apparatus includes: an imaging unit that applies a tag pulse capable of inverting a nuclear spin in a subject to a plurality of tag regions, at least a portion of which is set in an imaging region of the subject, and that thereafter performs imaging on the imaging region; and a reconstructing unit that reconstructs an image of the imaging region based on an echo signal obtained by the imaging.

According to another aspect of the present invention, there is provided that a magnetic resonance imaging method includes the steps of: applying a tag pulse capable of inverting a nuclear spin in a subject to a plurality of tag regions, at least a portion of which is set in an imaging region of the subject, and thereafter performing imaging on the imaging region; and reconstructing an image of the imaging region based on an echo signal obtained by the imaging.

According to yet another aspect of the present invention, there is provided that a magnetic resonance imaging apparatus includes: an imaging unit that applies a tag pulse capable of inverting a nuclear spin in a subject to a plurality of tag regions which are set outside an imaging region of the subject, and that thereafter performs imaging on the imaging region; and a reconstructing unit that reconstructs an image of the imaging region based on an echo signal obtained by the imaging.

According to yet another aspect of the present invention, there is provided that a magnetic resonance imaging method includes the steps of: applying a tag pulse capable of inverting a nuclear spin in a subject to a plurality of tag regions which are set outside an imaging region of the subject, and thereafter performing imaging on the imaging region; and reconstructing an image of the imaging region based on an echo signal obtained by the imaging.

DETAILED DESCRIPTION OF EXEMPLARY EMBODIMENTS

Figure 1:
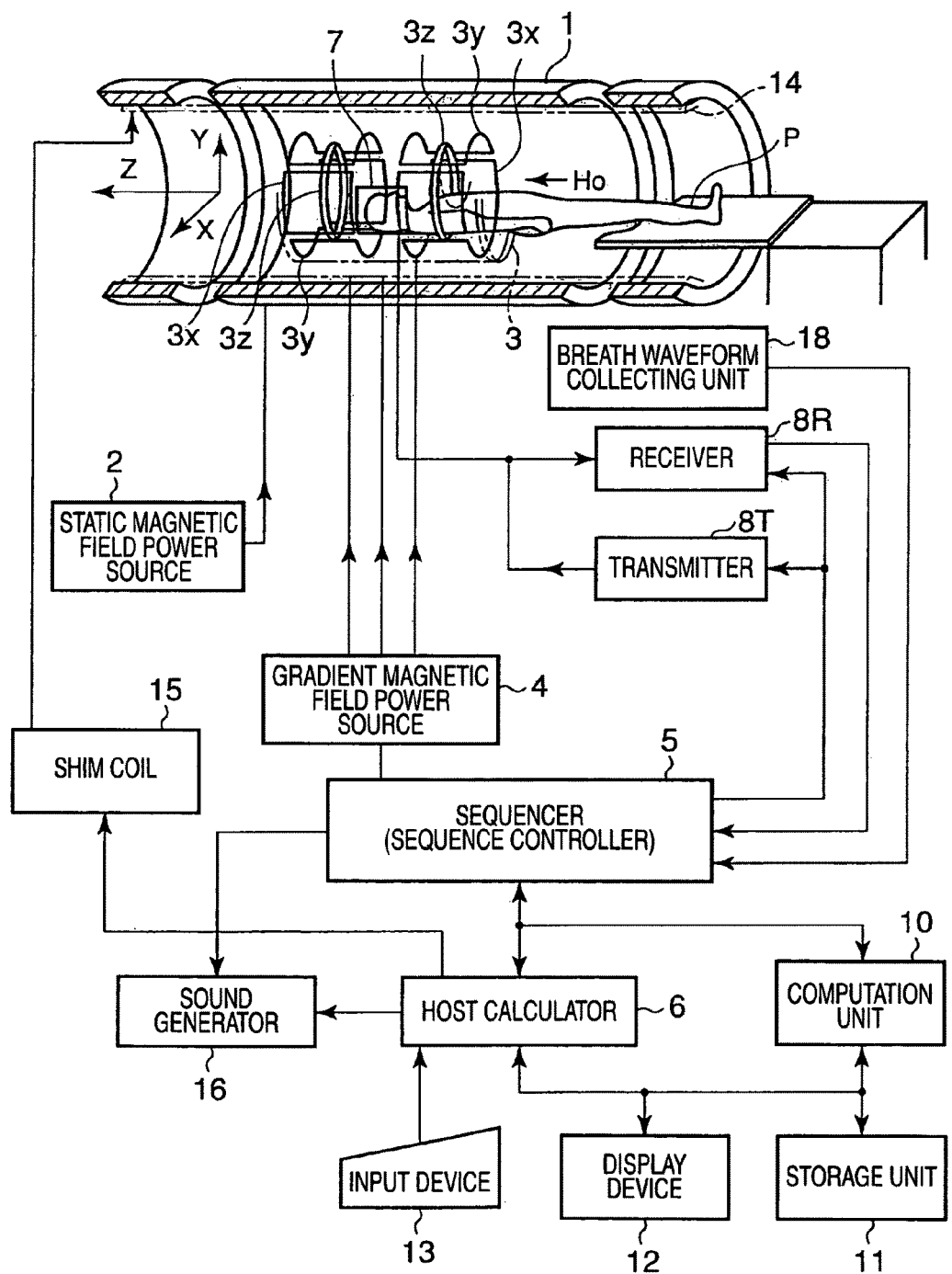
FIG. 1 is a block diagram showing the configuration of a magnetic resonance imaging apparatus according to a first embodiment of the present invention.

Hereinafter, embodiments of the present invention will be described with reference to the drawings. In the following description, those components having substantially similar functions and configurations will be denoted by the same reference numerals, and redundant description thereof will be omitted unless necessary.

First Embodiment

FIG. 1 is a block diagram showing the configuration of a magnetic resonance imaging apparatus according to a first embodiment of the present invention. As shown in the drawing, the magnetic resonance imaging apparatus includes a bed on which a patient P as a subject lies, a static magnetic field generator for generating a static magnetic field, a gradient magnetic field generator for adding positional information to the static magnetic field, a transmitter/receiver for transmitting/receiving a radio-frequency signal, a control/computation unit that controls the whole system and reconstructs an image, a breath waveform acquisition unit that measures a breath waveform signal as a signal representing the waveform of a breath cycle of the subject P, and a breath-hold instruction unit that instructs the subject P to hold breath.

The static magnetic field generator includes a superconducting magnet 1 and a static magnetic field power supply 2 for supplying electric current to the magnet 1. The static magnetic field generator generates a static magnetic field $H_0$ in an axial (Z-axis) direction of a cylindrical aperture portion (diagnostic space) into which the subject P is freely inserted. A shim coil 14 is provided to the magnet portion. The shim coil 14 is supplied with electric current from the shim coil power supply 15 under the control of a host computer described later, the electric current increasing the uniformity of the static magnetic field. The bed is configured such that a top board on which the subject P lies is moved into and out of the aperture portion of the magnet 1.

The gradient magnetic field generator includes a gradient magnetic field coil unit 3. The gradient magnetic field coil unit 3 includes three sets of coils $3x$, $3y$, and $3z$ capable of generating gradient magnetic fields in mutually perpendicular, X, Y, and Z-axis directions. The gradient magnetic field generator includes a gradient magnetic field power supply 4 for supply electric current to the coils $3x$ to $3z$. The gradient magnetic field power supply 4 supplies the coils $3x$ to $3z$ with a pulsating current that generates a gradient magnetic field under the control of a sequencer 5 described later.

By adjusting the pulsating current supplied from the gradient magnetic field power supply 4 to the coils $3x$ to $3z$, it is possible to synthesize the gradient magnetic fields in the respective physical axis directions, i.e., the X, Y, and Z directions to thereby arbitrarily set the respective, mutually perpendicular, logical axis directions of a slice direction gradient magnetic field Gs, a phase encoding direction gradient magnetic field Ge and a readout direction (frequency encoding direction) gradient magnetic field Gr. The respective gradient magnetic fields Gs, Ge and Gr in the slice direction, phase encoding direction and readout direction are superposed on the static magnetic field $H_0$.

The transmitter/receiver includes an RF coil 7 that is disposed at the vicinity of the subject P in an imaging space of the magnet 1, and a transmitter 8T and a receiver 8R, which are connected to the RF coil 7. The transmitter 8T and the receiver 8R are operated under the control of the sequencer 5 described later. The transmitter 8T supplies the RF coil 7 with RF pulses having the Larmor frequency for causing nuclear magnetic resonance (NMR). The receiver 8R takes in echo signals (radio-frequency signals) received by the RF coil 7, carries out various kinds of signal processing, such as pre-amplification, intermediate-frequency conversion, phase detection, low-frequency amplification, and filtering, on the echo signals, and then subjects the resulting signals to A/D conversion to thereby generate echo data (raw data) having a digital quantity corresponding to the echo signals.

The control/computation unit includes the sequencer 5 (also referred to as a sequence controller), a host computer 6, a computation unit 10, a storage unit 11, a display unit 12, an input unit 13, and a sound generator 16. Of them, the host computer 6 has a function of providing the sequencer 5 with pulse sequence information and managing the operations of the entire system in accordance with software procedures memorized therein.

The host computer 6 performs an imaging scan subsequent to preparatory tasks such as a positioning scan. The imaging scan is a scan for collecting a set of echo data necessary for the image reconstruction. Moreover, the host computer 6 determines a scan sequence in a non-contrast MRA based on a tag region, which will be described later.

As to the pulse sequences, a two-dimensional (2D) scan or a three-dimensional (3D) scan can be used. Examples of the form of pulse trains available to those scans include an SE (spin echo) method, an FSE (fast spin echo) method, an FASE (fast asymmetric spin echo) method, an EPI (echo planar imaging) method, a coherent gradient echo (True SSFP, True FISP, and balanced FFE) method, and others.

The sequencer 5 includes a CPU and a memory. For example, the sequencer 5 stores therein the pulse sequence information on the non-contrast MRA, delivered from the host computer 6 and controls operations of the gradient magnetic field power supply 4, the transmitter 8T, and the receiver 8R in accordance with the information. Moreover, the sequencer 5 temporarily stores therein the echo data output from the receiver 8R and transmits the data to the computation unit 10. The pulse sequence information is the whole information necessary to operate the gradient magnetic field power supply 4, the transmitter 8T, and the receiver 8R in accordance with a series of pulse sequences, and includes information regarding, for example, the intensity of the pulsating current applied to the coils 3x, 3y and 3z, application time, and application timing.

The echo data output by the receiver 8R is input to the computation unit 10 through the sequencer 5. The arithmetical unit 10 maps the echo data in a Fourier space (also referred to as a k space or a frequency space) set in an internal memory. The arithmetical unit 10 performs for each set of the mapped echo data a two-dimensional or three-dimensional Fourier transformation so as to reconstruct image data in the real space. The arithmetical unit 10 can also perform synthesizing processing and difference computing processing for image data as necessary.

The synthesizing processing includes addition of image data of a plurality of two-dimensional frames every corresponding pixel, and maximum intensity projection (MIP) processing or minimum intensity projection processing for selecting a maximum value or minimum value in a viewing direction for three-dimensional data. Another example of the synthesizing processing may be to align the axes of a plurality of frames on the Fourier space to synthesize them with the echo data for one frame without changing the echo data. In addition, the addition processing includes simple addition processing, averaging processing, weighting addition processing, etc.

The storage unit 11 can store the image data subjected to the above-mentioned synthesizing processing and difference processing as well as the reconstructed image data. The display unit 12 displays images under the control of the host computer 6. A display device such as a liquid crystal display can be used as the display 12. The input unit 13 is an I/F that allows an operator to input various kinds of information such as imaging conditions desired by the operator, the pulse sequence, and information regarding the synthesizing processing and difference computing to the host computer 6. Moreover, the input unit 13 has an I/F that allows setting or changing the position, size, and the like of single or plural tag region(s), which will be described later.

The breath-holding instruction unit includes a sound generator 16. The sound generator 16 can generate audible messages that inform the starting and ending of breath holding in accordance with the instructions from the host computer 6.

The breath waveform acquisition unit includes a breath waveform collecting unit 18 that measure an internal motion of a subject, for example, to acquire a breath waveform of the patient and outputs the acquired breath waveform to the host computer 6 and the sequencer 5. The breath waveform obtained by the breath waveform collecting unit 18 is used by the sequencer 5 when performing the imaging scan. This makes it possible to properly set exhalation synchronization timing by the breath synchronization method, and the imaging scan can be performed based on this synchronization timing to collect data.

[Non-Contrast MRA Function]

Next, a non-contrast MRA function of the magnetic resonance imaging apparatus will be described. This function is to apply an IR pulse to perform labeling (or tagging) on a region of a subject in both time and space domain to thereby visualize an MR signal derived from blood or the like with higher or lower intensity than that of signals derived from other regions. At this time, a time lapse (hereinafter, referred to as "TI") elapsed from the application time of a tagging IR pulse to the application time of the first RF pulse is adjusted to control the state of blood flowing into the region from a certain portion of the patient body and a visualization method (for example, contrast) of tissues.

An imaging method used in this function is often referred to as a Time-SLIP (Time-Spatial Labeling Inversion Pulse) method since the method applies an IR pulse to thereby label a region of the subject in both time and space domain. The region (or a region on an image corresponding to this region) of the subject, to which the IR pulse is applied and which is subjected to tagging will be referred to as a tag region.

[Non-Contrast MRA Using Single Tag Region]

Figure 2:
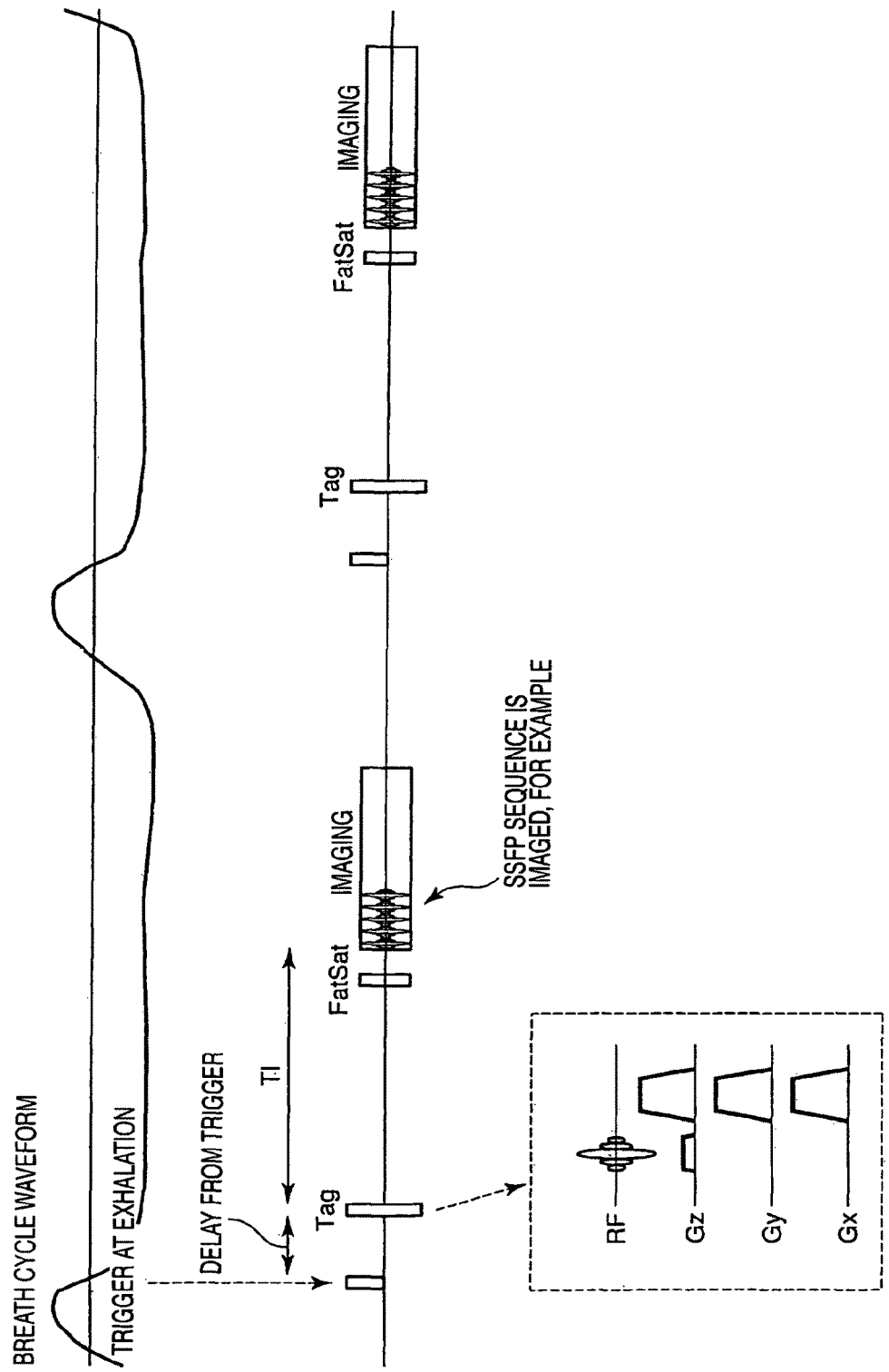
FIG. 2 is a diagram showing an example of a scan sequence in a non-contrast MRA in which a single tag region is employed.

FIG. 2 is a diagram showing an example of a scan sequence in a non-contrast MRA in which a single tag region is employed. As an example, description will be given for a case where a blood flow in the renal artery is visualized as an RF signal without the aid of a contrast agent by using the sequence shown in FIG. 2.

Referring to FIG. 2, a sequence in which imaging is performed using a three-dimensional SSFP (Steady State Free Precession) method is illustrated. However, the imaging method is not limited to this, but the imaging may be performed by other scan sequences such as a three-dimensional FSE (Fast Spin Echo) method or a three-dimensional FASE (Fast Advanced Spin Echo) method. Moreover, an image collection form may be either a form wherein a single shot is taken or a form wherein multiple shots are taken. For example, when the example shown in FIG. 2 is the sequence based on a single-shot, three-dimensional SSFP method, the first slice encoding is performed in the first imaging I, and the second slice encoding is performed in the subsequent imaging II. On the other hand, when the example shown in FIG. 2 is the sequence based on a multi-shot (two-shot), three-dimensional SSFP method, the first shot for the first slice encoding is performed in the first imaging I, and the second shot for the first slice encoding is performed in the subsequent imaging II.

First, the sequencer 5 applies an IR pulse to a predetermined tag region (see FIG. 3) that is set over the branch portions from the liver, for example, at a timing with a predetermined delay time from an exhalation start time to thereby perform tagging. By this tagging, it is possible to suppress the MR signals derived from the liver and the kidney within the tag region and from other substantial portions, the portal vein and the venous system.

Next, the sequencer 5 performs an imaging scan (a scan for collecting data necessary for image reconstruction) after a predetermined time lapse TI from the tagging (i.e., application of the IR pulse). The above operations may be repeated depending on necessity. The computation unit 10 performs image reconstruction by the use of the MR signal acquired through the imaging scan to thereby generate a time-serial MR image.

Figure 3:
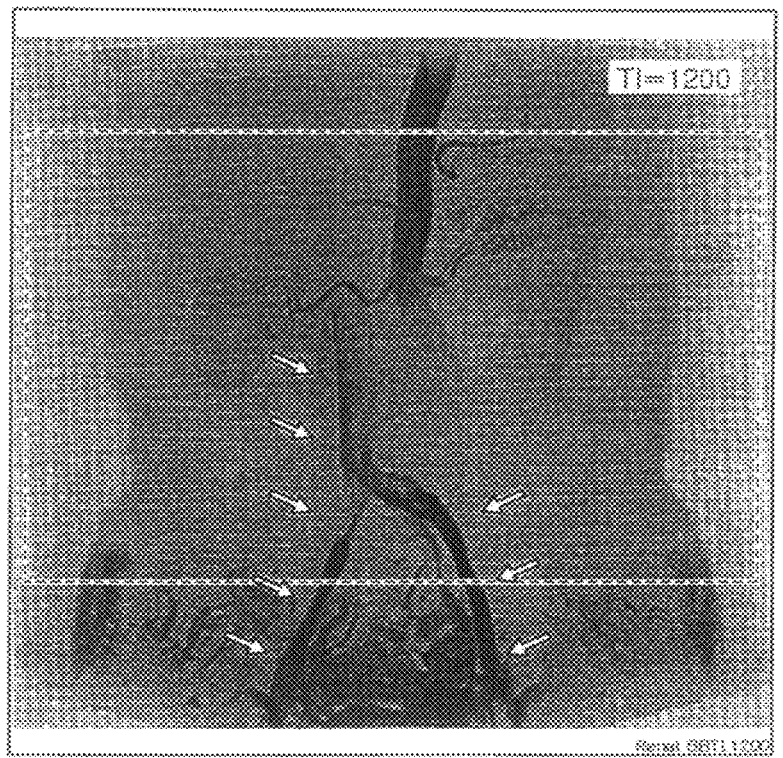
FIG. 3 is a diagram showing an example of an MR image acquired using the pulse sequence shown in FIG. 2.

According to the above-described scan sequence, during a time period TI, the blood which is not subjected to signal suppression by the IR pulse flows from the renal artery at the upstream side thereof outside the tag region into the tag region which is subjected to signal suppression by the IR pulse. Since the imaging is performed on an imaging region after the time lapse TI, as shown in FIG. 3, for example, it is possible to obtain an MR image in which the blood of the renal artery flowing into the tag region during the time period TI is visualized with higher intensity (higher brightness) than the surroundings.

Moreover, FIG. 2 shows the example of the scan sequence in which a FatSat pulse (Fat Saturation pulse) is used. The FatSat pulse is assumed that it is not applied in a space-selective manner. The fat saturation by the FatSat pulse is not essential to the non-contrast MRA according to the present invention; therefore, it may be omitted depending on the necessity.

Figure 4:
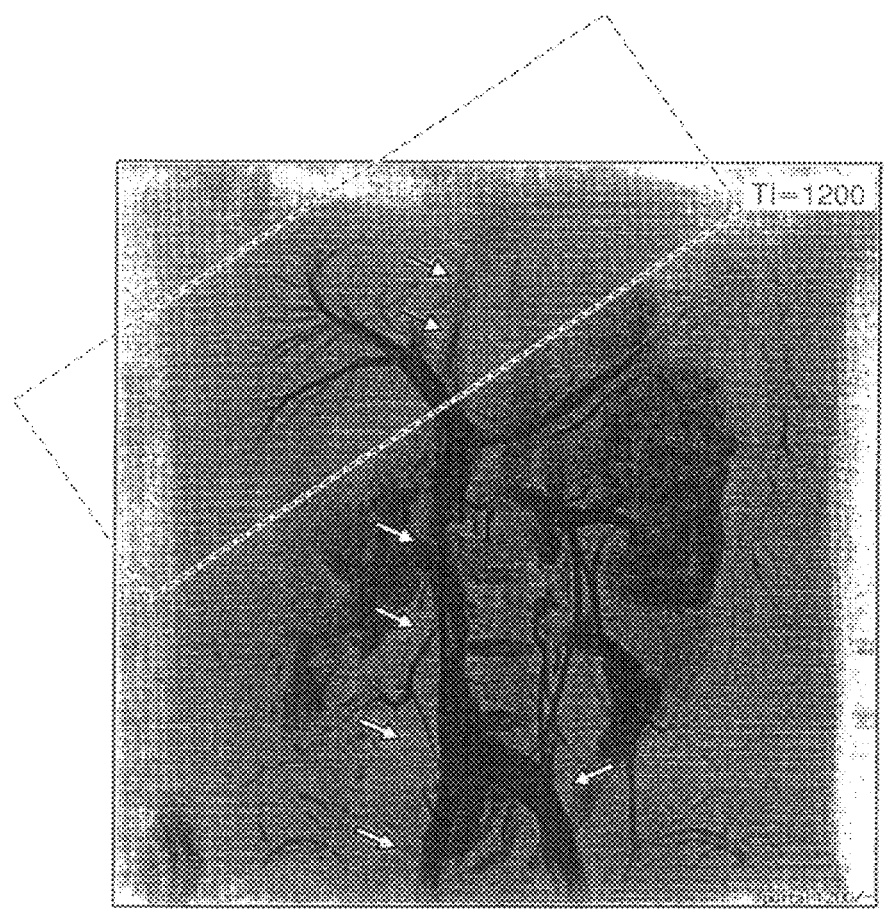
FIG. 4 is a diagram showing another example of an MR image acquired using the pulse sequence shown in FIG. 2.

FIG. 4 is a diagram showing another example of an MR image acquired using the pulse sequence shown in FIG. 2. According to this example, the tag region is set at the side of the liver and the heart to suppress the MR signal derived from within the tag region, whereby the blood flowing into the liver within the tag region from the outside of the tag region during the time period TI can be visualized with high intensity (high brightness).

Figure 5:
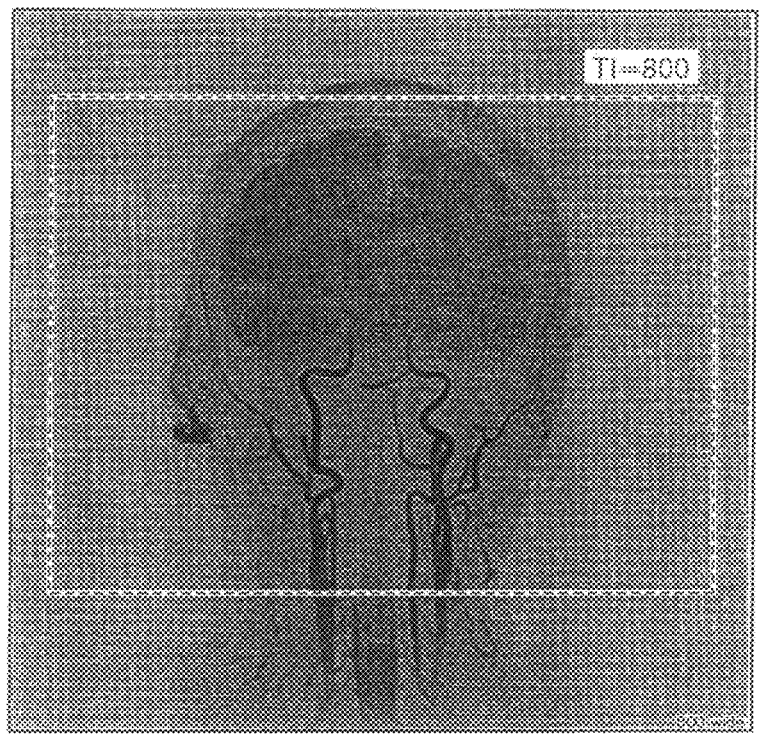
FIG. 5 is a diagram showing yet another example of an MR image acquired using the pulse sequence shown in FIG. 2.

FIG. 5 is a diagram showing yet another example of an MR image acquired using the pulse sequence shown in FIG. 2. According to this example, the tag region is set to the whole head part including the cerebral cortex to suppress the MR signal derived from within the tag region, whereby the blood flowing into the artery within the tag region from the outside of the tag region during the time period TI can be visualized with high intensity (high brightness).

In the examples described above, the IR pulse is applied once to the inside of the tag region to thereby suppress the MR signal derived from the tissues within the tag region, whereby the blood flowing into the artery within the tag region from the outside of the tag region during the time period TI can be visualized with high intensity (high brightness). However, the present invention is not limited to these examples, and the non-contrast MRA function of the present invention includes a variety of variations.

For example, a method may be used in which for the same imaging region, an MR image in which the tagging by the IR pulse is not performed, a plurality of MR images in which the position, size, or the like of the tag regions that are tagged by the IR pulse are changed, and the like may be collected to thereby perform difference computing processing based on the MR images. By doing this, it is possible to generate an image in which only the tagged blood flow is extracted or an image in which an MR signal derived from portions other than blood vessels is suppressed, without the aid of a contrast agent.

Moreover, a method can be used in which a first IR pulse (a pulse capable of inverting nuclear spin by 180 degrees) for spin excitation is applied to the entire imaging region, and after a predetermined time lapse (for example, 2 to 10 ms), a second IR pulse (similarly, a pulse capable of inverting nuclear spin by 180 degrees) for tagging of a tag region is applied to the imaging region. The time lapse between the application time of the first IR pulse and the application time of the second IR pulse is extremely short compared with the blood velocity. For this reason, the blood within the tag region is substantially simultaneously applied with the first and second IR pulses (both of which invert nuclear spin by 180 degrees), so the longitudinal magnetization thereof is returned to a substantially initial state, and after a predetermined time lapse (for example, TI), the blood flows into a region at the downstream side thereof where only the first IR pulse is applied. As a result, the blood having applied with both the first IR pulse and the second IR pulse is visualized as a region in which the MR signal has higher intensity than the tissue regions where only the first IR pulse is applied.

The variations in the non-contrast MRA described above are all applicable to the present invention. The second IR pulse is often referred to as "spatial-selective IR pulse" since it aims to select a tag region in the imaging region and perform tagging on the tag region. Meanwhile the first IR pulse is often referred to as "non-spatial-selective IR pulse" since it is not used for the above purposes. Thus, the latter pulse is freely turned on/off automatically or via a predetermined operation through the input unit 13 depending on the selected type of the non-contrast MRA.

[Non-Contrast MRA Using Plurality of Tag Regions]

For example, in the non-contrast MRA shown in FIG. 3, in which a single tag region is used, not only the blood flow of the renal artery that is to be diagnosed but also the ascending aorta are visualized with high intensity. This is because depending on portions of the subject, the blood may flow into the portion in multiple directions via a plurality of blood vessels. In a case where such a portion is included in the imaging region, it is difficult to label only the blood vessel that is to be diagnosed in a single tag region.

According to the non-contrast MRA function in which a plurality of tag regions are used, since a plurality of tag regions are used in the same imaging sequence, it is possible to selectively visualize only the blood vessel (blood flow) that is to be diagnosed as an RF signal while blood vessels that are not interested are not visualized. As a result, it is possible to facilitate the image observation and to enable recognition of portions hidden by the blood vessels that are not of interest.

Figure 6:
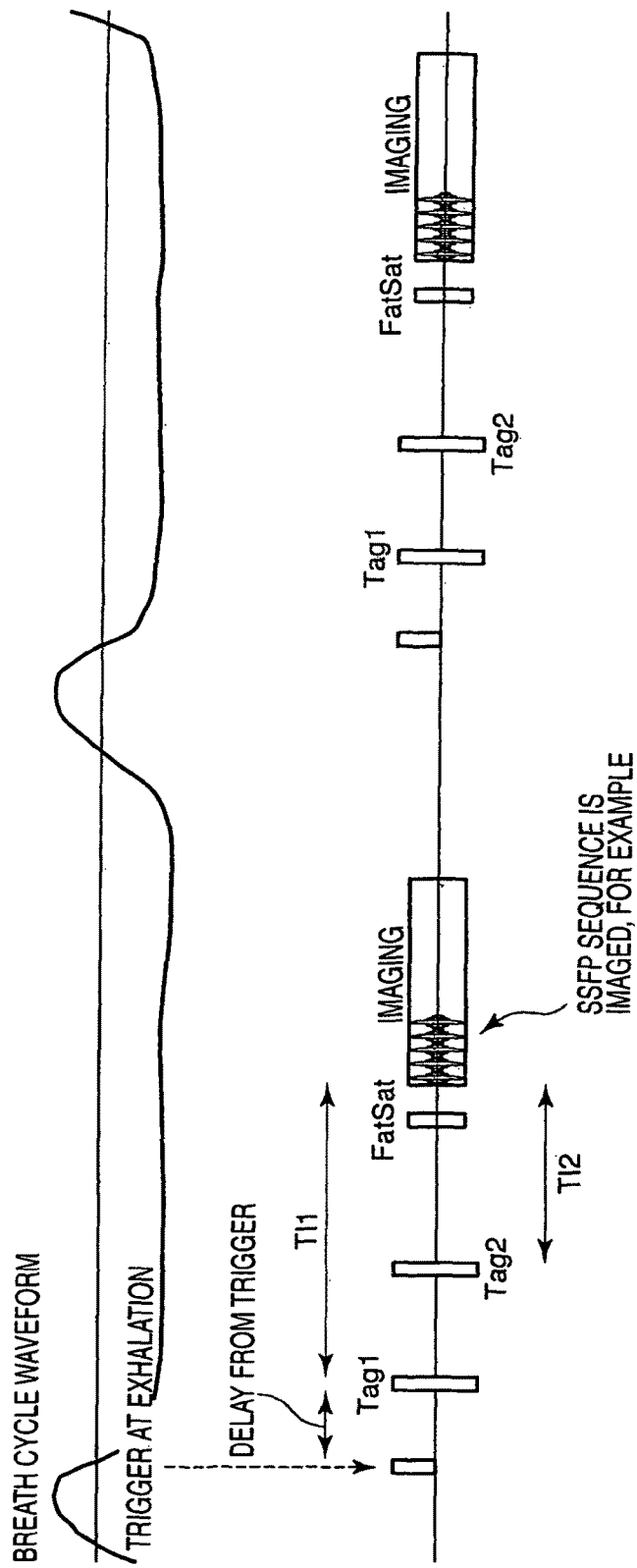
FIG. 6 is a diagram showing an example of a scan sequence in a non-contrast MRA in which a plurality of tag regions is employed.
Figure 7:
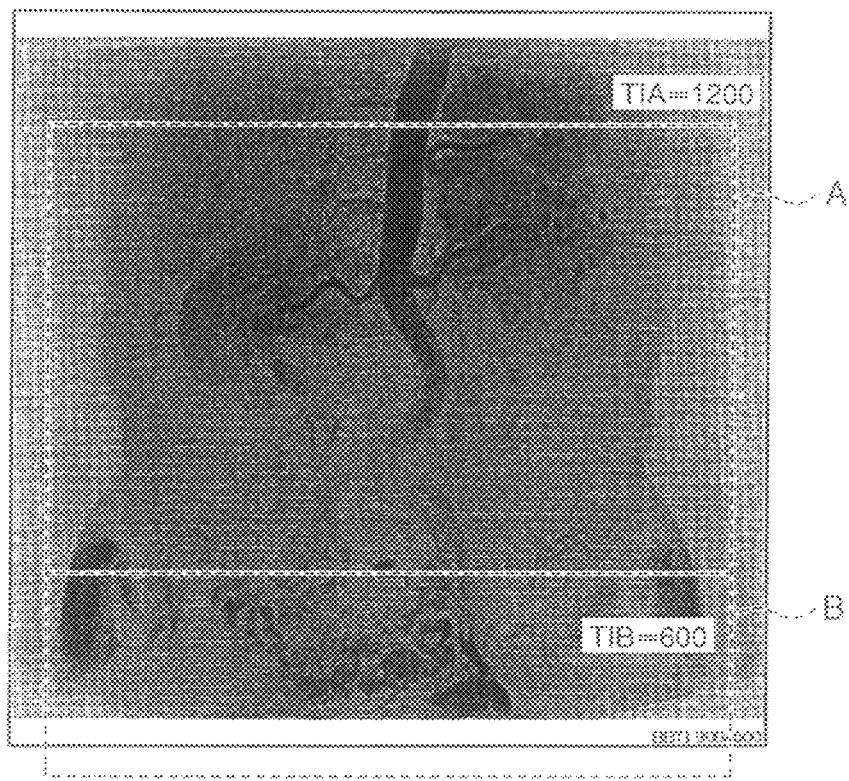
FIG. 7 is a diagram showing a tag region A set by the use of a positioning image and a tag region B disposed at the upstream side of the ascending vena cava relative to the tag region A.

FIG. 6 is a diagram showing an example of a scan sequence in a non-contrast MRA in which a plurality of tag regions is employed. As an example, description will be given for a case where only the blood flow of the renal artery is visualized as an RF signal without the aid of a contrast agent by using the sequence shown in FIG. 6. In FIG. 6, similar to FIG. 2, although the imaging is performed using the SSFP sequence, other scan sequences may be used such as a three-dimensional FSE method or a three-dimensional FASE method. Moreover, it is assumed that as the tag regions, two tag regions shown in FIG. 7 are set including: a tag region A and a tag region B disposed at the upstream side of the ascending vena cave relative to the tag region A. However, the number of tag regions is not limited to two, but three or more tag regions may be set.

First, the sequencer 5 applies an IR pulse to a predetermined tag region A that is set over the branch portions from the liver at a timing with a first predetermined delay time TD1 from an exhalation start time to thereby perform tagging. By this tagging, it is possible to suppress the MR signals derived from the liver and the kidney within the tag region A and from other substantial portions, the portal vein and the venous system.

Subsequently, the sequencer 5 applies an IR pulse to the tag region B that is disposed at the upstream side of the ascending vena cave relative to the tag region A at a timing with a second predetermined delay time TD2 (for example, 600 ms) from the application time of the IR pulse to the tag region A to thereby perform tagging. By this tagging, it is possible to suppress the MR signals derived from the substantial portions and the blood within the tag region B.

Next, the sequencer 5 performs an imaging scan after a predetermined time lapse TIA (for example, 1200 ms) from the application time of the IR pulse to the tag region A or after a predetermined time lapse TIB (for example, 600 ms) from the application time of the IR pulse to the tag region B. The above operations may be repeated depending on necessity. The computation unit 10 performs image reconstruction by the use of the MR signal acquired through the imaging scan to thereby generate a time-serial MR image.

According to the above-described scan sequence, during a time period TIA, the blood which is not subjected to signal suppression by the IR pulse applied to the tag region A flows from the renal artery at the upstream side thereof outside the tag region A into the tag region A which is subjected to signal suppression by the IR pulse. Moreover, during a time period TIB, the blood in the ascending vena cave which is subjected to signal suppression by the IR pulse applied to the tag region B flows into the tag region A which is similarly subjected to signal suppression by the IR pulse. The imaging for collecting diagnostic images is performed after the time lapse TIA (and the time lapse TIB). For this reason, as shown in FIG. 7, for example, it is possible to obtain an MR image in which the MR signals derived from the ascending vena cava is suppressed, and in which only the blood of the renal artery flowing into the tag region A during the time period TI is visualized with higher intensity (higher brightness) than the surroundings, and the aorta at the downstream side hidden by the ascending vena cave can be observed.

Figure 8:
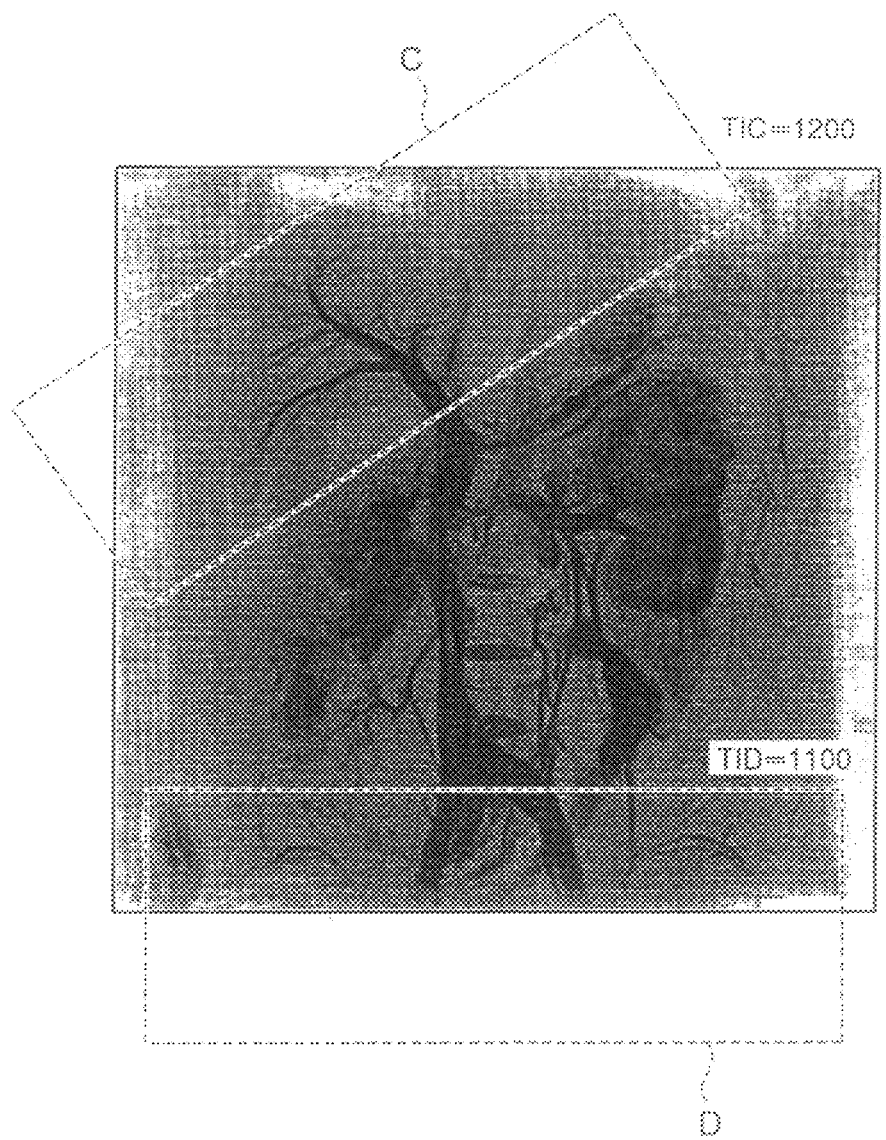
FIG. 8 is a diagram showing another example of the scan sequence in a non-contrast MRA in which two tag regions (a tag region C set at the side of the liver and the heart and a tag region D disposed at the upstream side of the ascending aorta) are employed in the pulse sequence shown in FIG. 6.

FIG. 8 is a diagram showing another example of the scan sequence in a non-contrast MRA in which two tag regions (a tag region C set at the side of the liver and the heart and a tag region D disposed at the upstream side of the ascending aorta) are employed in the pulse sequence shown in FIG. 6. According to this example, during a time period TIC (for example, 1200 ms), the blood which is not subjected to signal suppression by the IR pulse applied to the tag region C flows from the portal vein at the upstream side outside the tag region C into the tag region C which is subjected to signal suppression by the IR pulse. Moreover, during a time period TID (for example, 1100 ms), the blood in the ascending vena cave which is subjected to signal suppression by the IR pulse applied to the tag region D flows into the tag region C which is similarly subjected to signal suppression by the IR pulse. Therefore, by performing the imaging for collecting diagnostic images after the time lapse TIC (and the time lapse TID), it is possible to obtain an MR image in which the MR signals derived from the ascending vena cave is suppressed, and in which only the blood flowing into the portal vein and the liver within the tag region C during the time period TI is visualized with higher intensity (higher brightness) than the surroundings.

Figure 9:
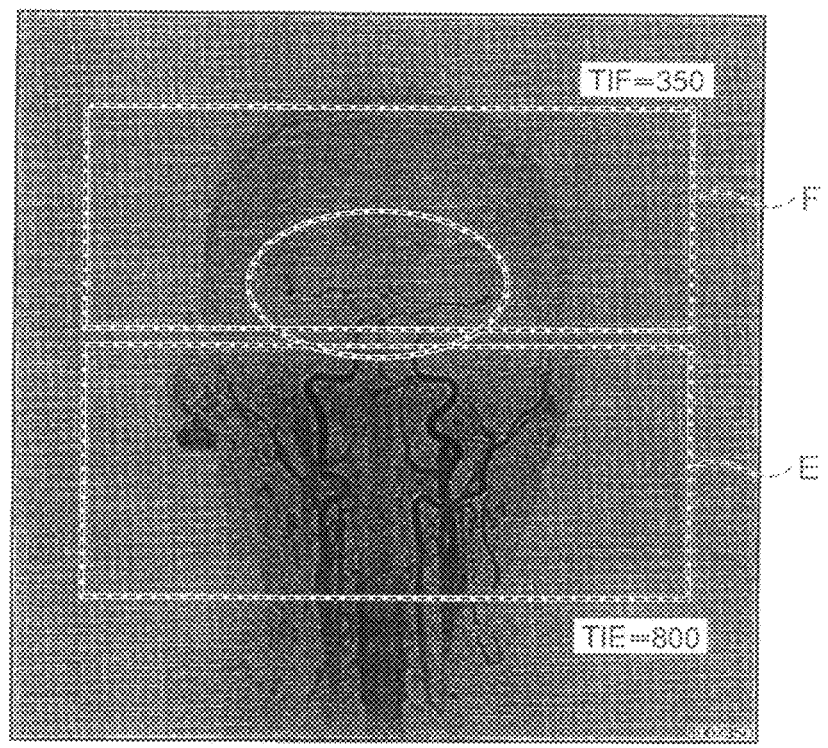
FIG. 9 is a diagram showing another example of an MR image acquired using the pulse sequence shown in FIG. 6.

FIG. 9 is a diagram showing another example of the scan sequence in a non-contrast MRA in which two tag regions (a tag region E disposed at the upstream side of an artery and a tag region F set in a region of the cerebrum) are employed in the pulse sequence shown in FIG. 6. According to this example, during a time period TI1 (for example, 800 ms), the blood which is not subjected to signal suppression by the IR pulse applied to the tag region E flows from the artery at the upstream side outside the tag region E into the tag regions E and F which are subjected to signal suppression by the IR pulse. Moreover, during a time period TI2 (for example, 350 ms), the MR signals derived from the cerebral tissues are suppressed by the IR pulse applied to the tag region F. Therefore, by performing the imaging for collecting diagnostic images after the time lapse TI1 (and the time lapse TI2), it is possible to obtain an MR image in which the arteries in the brain (see the elliptical range in FIG. 9) are visualized with high intensity (high brightness) without being hidden by the cerebral tissues.

[Operation]

Next, operations of the magnetic resonance imaging apparatus according to a process (non-contrast MRA process) enabled by the non-contrast MRA function will be described.

Figure 10:
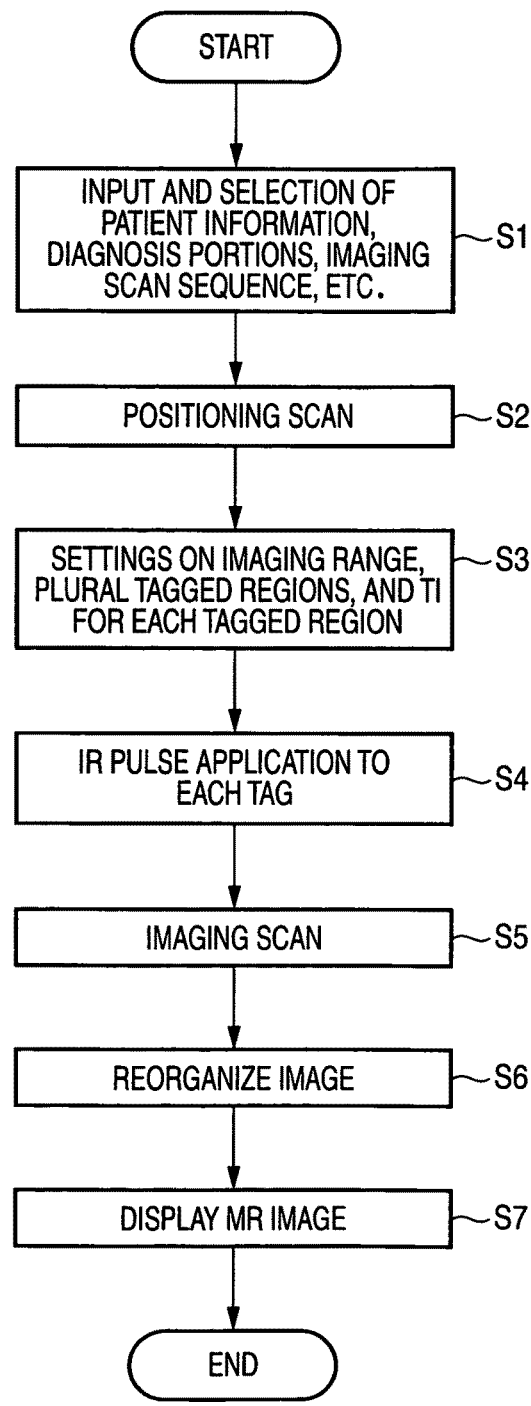
FIG. 10 is a flow chart illustrating the flow of a non-contrast MRA process.

FIG. 10 is a flow chart illustrating the flow of a non-contrast MRA process. Hereinafter, as an example, description will be given, with reference to the flow chart, for a case where only the blood flow of the renal artery is visualized as an RF signal without the aid of a contrast agent by using the sequence shown in FIG. 6.

As shown in FIG. 10, first, when input and selection of patient information, diagnostic portions, scan sequence for use in the image, and the like are performed through the input unit 13 (step S1), the host computer 6 performs a positioning scan in order to acquire a positioning image for use in setting of an imaging range and a tag region (step S2).

Next, by using the acquired positioning image and in accordance with the information input through the input unit 13, the imaging range as shown in FIG. 7 and the time period TI (TIA=1200 ms and TIB=600 ms) for each of the tag regions A and B are set (step S3).

Next, the sequencer 5 performs non-contrast MRA in accordance with a scan sequence (see FIG. 6), which is determined by the imaging range, the plural tag regions, and the time lapse TI for each of the tag regions. Specifically, a first IR pulse is applied to the tag region A at a timing with a predetermined delay time from an exhalation start time as a trigger, and a second IR pulse is applied to the tag region B after a predetermined delay time from the application time of the first IR pulse (step S4). Then, the imaging scan is performed in accordance with a predetermined sequence after the time lapse TIA from the application time of the first IR pulse (or after the time lapse TIB from the application time of the second IR pulse) (step S5).

Next, the computation unit 10 performs image reconstruction by the use of the MR signal acquired through the imaging to thereby generate an MR image (step S6). The display unit 12 displays the generated MR image as a moving picture or a still image (step S7).

First Application Example: Number, Position and Size of Tag Region

In the non-contrast MRA function of this application example, the number, position, shape, and size of the tag regions are arbitrarily controlled. Therefore, three or more tag regions may be set for one collection of the MR image, and a plurality of tag regions in which the direction or size is different may be set. Moreover, the tag regions may be set such that they overlap with each other.

Figure 11:
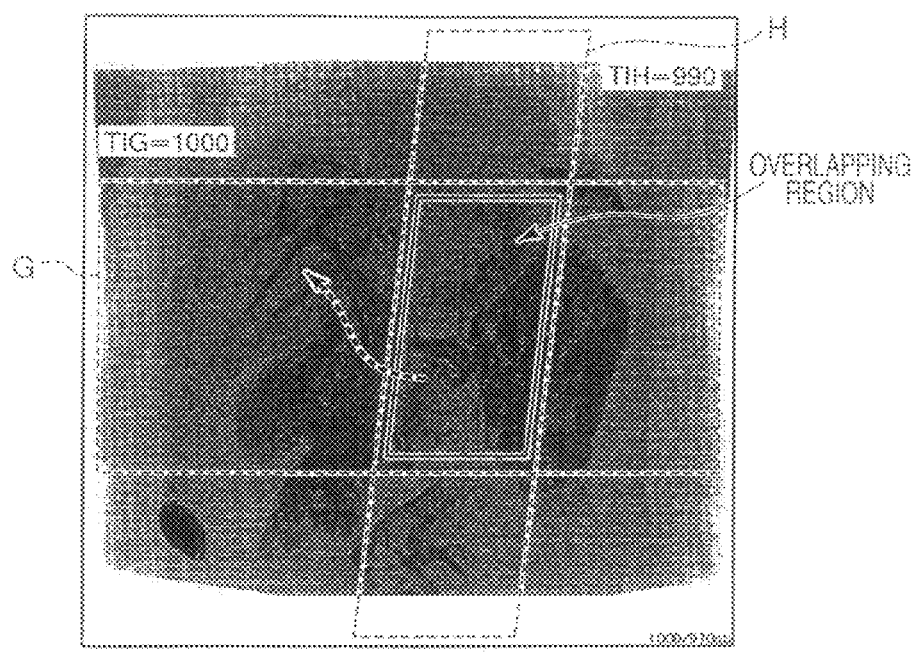
FIG. 11 is a diagram showing an example of an MR image obtained by setting a tag region G (TIG=1000 ms) and a tag region H (TIH=990 ms) so as to cross each other.

FIG. 11 is a diagram showing an example of an MR image obtained by setting a tag region G (TIG=1000 ms) and a tag region H (TIH=990 ms) so as to cross each other. Like this example, when two tag regions are set to cross each other and the time lapses TI of both regions are similar or equal, the overlapping region (crossing region) of the two tag regions is applied twice and substantially simultaneously with the 180-degree inversion pulses (spin excitation pulses); therefore the nuclear spins in the overlapping region will return to their initial state. Therefore, an MR image can be obtained in which only the blood flowing out from the overlapping region of the two tag regions is visualized as an RF signal, and in which an MR image derived from the substantial portions disposed in other tag regions where they do not overlap is suppressed.

Figure 12:
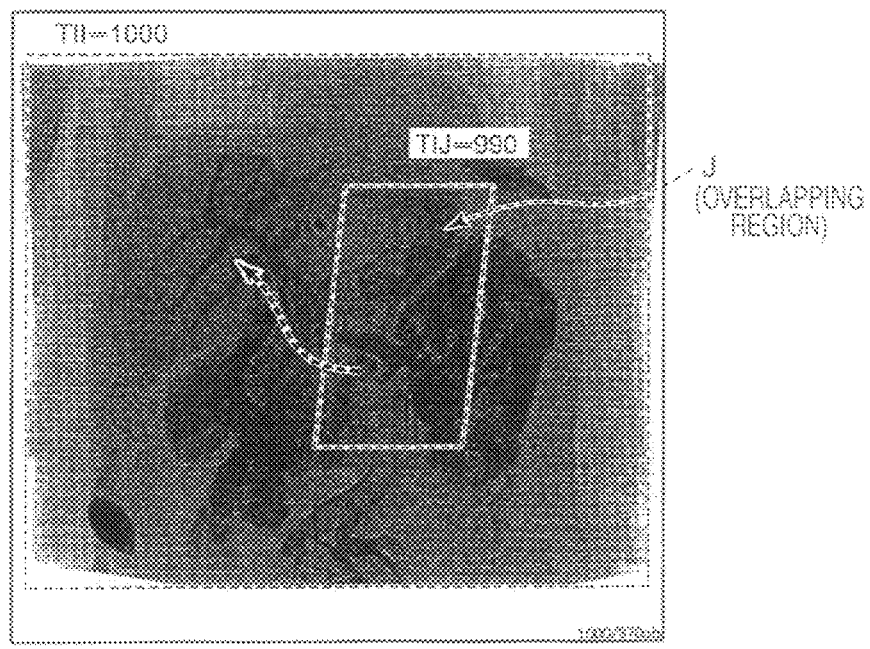
FIG. 12 is a diagram showing an example of an MR image obtained by setting a tag region I (TII=1000 ms) and a tag region J (TIJ=990 ms) so as to overlap with each other.

FIG. 12 is a diagram showing an example of an MR image obtained by setting a tag region I (TII=1000 ms) and a tag region J (TIJ=990 ms) so as to overlap with each other. The tag region J, which is an overlapping region, is applied twice and substantially simultaneously with the 180-degree inversion pulses (spin excitation pulses); therefore the nuclear spins in the overlapping region will return to their initial state. Therefore, an MR image can be obtained in which only the blood flowing out from the tag region J is visualized as an RF signal, and in which an MR image derived from the substantial portions disposed in other tag regions where they do not overlap is suppressed.

Second Application Example: TI Control by Flip Angle

Figure 13:
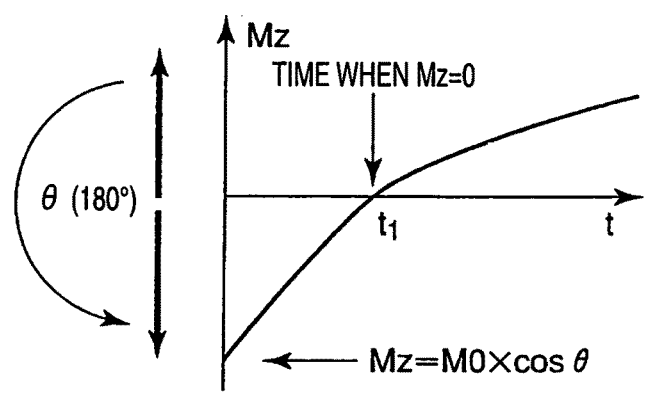
FIG. 13 is a diagram showing a change with time, of longitudinal magnetization Mz when an IR pulse has a flip angle of 180 degrees.

FIG. 13 is a diagram showing a change with time, of longitudinal magnetization Mz when an IR pulse has a flip angle of 180 degrees. As shown in the drawing, when the flip angle is set to 180 degrees, it takes time of t1 until the longitudinal magnetization Mz becomes zero (Mz=0).

However, in the case of imaging that uses the breath synchronization method, for example, the imaging sequence is performed after a time lapse TI from a trigger point. For this reason, when the time lapse TI is long, the time difference from the breath synchronization trigger increases, thereby increasing the possibility that the precision of the breath synchronization is lowered.

To solve such a problem, according to the non-contrast MRA function of this application example, the flip angle θ by the tagging IR pulse is controlled within the range of 90 degrees≤θ≤180 degrees, for example, in order to arbitrarily adjust the time TI at which the longitudinal magnetization becomes zero.

Figure 14:
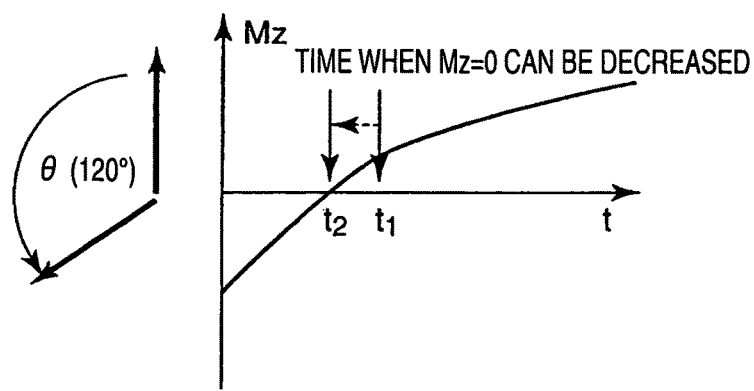
FIG. 14 is a diagram showing a change with time, of longitudinal magnetization Mz when an IR pulse has a flip angle of 120 degrees, for example.

FIG. 14 is a diagram showing a change with time, of longitudinal magnetization Mz when an IR pulse has a flip angle of 120 degrees, for example. As shown in the drawing, when the flip angle is set to 120 degrees, it is possible to shorten the time t2 (<t1) until the longitudinal magnetization Mz becomes zero (Mz=0). By doing this, it is possible to shorten the time TI, and an MR image can be obtained with high reliability in synchronism with the gating even when a patient is able to hold breath for only a short time, for example.

It is to be noted that the time when Mz=0 may be calculated from the TI of the tissue that is to be tagged and the flip angle θ by the IR pulse by means of an analytic method that uses the Bloch equation.

Third Application Example: TI Setting Assistance Function

The length of the TI is usually determined based on the velocity of the blood flow that is to be visualized and the recovery time of the substantial longitudinal magnetization that is to be subjected to signal suppression by the IR pulse. However, due to an individual difference, the TI determined by the above criteria is sometimes unable to provide appropriate visualization of the blood flow that is to be diagnosed.

In order to be able to visualize the blood flow that is to be diagnosed even in such a case, the magnetic resonance imaging apparatus according to this application example provides a TI setting assistance function. This function is to perform non-contrast MRA on the respective tag regions using a plurality of TI setting values to thereby provide an MR image for each of the TI setting values as TI setting assistance information.

Figure 15:
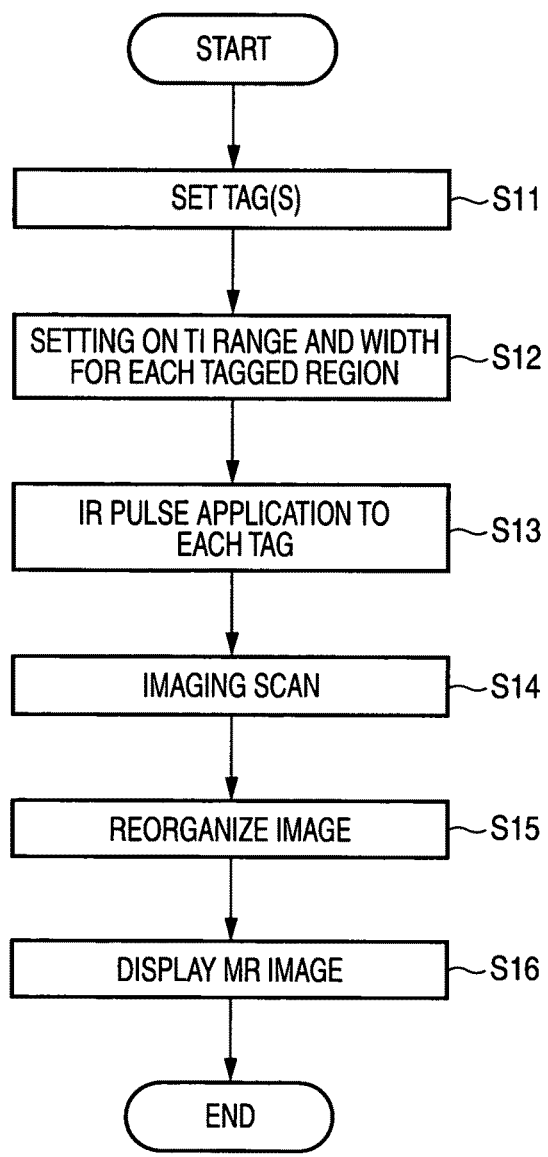
FIG. 15 is a flow chart illustrating the flow of a process enabled by a TI setting assistance function (a TI setting assistance process).

FIG. 15 is a flow chart illustrating the flow of a process enabled by a TI setting assistance function (a TI setting assistance process). As shown in the drawing, a plurality of tag regions is set via the input unit 13 (step S11). Although a plurality of tag regions are illustrated to concretize the description, a single tag region may be used.

Next, when a TI range (for example, upper and lower limits of the TI) for each of the tag regions and a TI width are set via the input unit 13, the host computer 6 sets a plurality of TI setting values to the respective tag regions based on the TI range and width (step S12). Specifically, when the TI is set for a tag region such that the upper limit is 1200 ms, the lower limit is 600 ms, and the TI width is 10 ms, the host computer 6 sets a plurality of TI setting values: 600 ms, 610 ms, 620 ms, . . . , 1190 ms, and 1200 ms, with an interval of 10 ms within the range of 600 ms≤TI (ms)≤1200 ms, on the tag region based on the input values.

Next, the sequencer 5 performs non-contrast MRA in accordance with the above-described sequence by the use of the respective TI setting values (steps S13 and S14). At this time, from the viewpoint of processing efficiency, it is desirable to perform an imaging scan so that the scan acquires a minimal image (for example, a two-dimensional image represented as a positioning image) necessary for making determination as to whether the TI setting values are appropriate or not.

Next, the computation unit 10 performs image reconstruction by the use of the respective MR signals acquired through the imaging corresponding to the respective TI setting values to thereby generate an MR image for each of the TI setting values (step S15). The display unit 12 displays the generated MR images for each of the TI setting values in a predetermined form (step S16). Then, a user can observe the respective MR images for each of the TI setting values and select an MR image in which the blood flow that is to be observed is appropriately visualized, whereby a suitable TI is automatically set.

Fourth Application Example: Variation in Differential Process

According to the magnetic resonance imaging apparatus of this application example, when non-contrast MRA is performed using a plurality of tag regions, it is possible to generate a variety of differential images by difference computing processing based on a combination of ONs and OFFs of the spatial-selective pulses.

For example, in the example shown in FIG. 4 where tag regions A and B are set, the following differential images can be generated. That is, a differential image can be generated by the use of an MR image obtained by performing tagging on the tag regions A and B and an MR image in which the tagging IR pulse is not applied to the same imaging region. Moreover, another differential image can be generated by the use of an MR image obtained by performing tagging on the tag regions A and B and an MR image obtained by performing the tagging on only the tag region A for the same imaging region. Furthermore, another differential image can be generated by the use of an MR image obtained by performing tagging on the tag regions A and B and an MR image obtained by performing the tagging on only the tag region B for the same imaging region.

Advantages

According to the configuration described above, the following advantages can be provided.

According to the magnetic resonance imaging apparatus of the present embodiment, it is possible to arbitrarily set the number, position, and size of the tag regions. For this reason, by appropriately setting the number, position, size, shape, and the like of the tag regions in the non-contrast MRA, it is possible to appropriately perform tagging on the MR signals derived from a blood vessel or the like that is to be diagnosed in both time and spatial domain. As a result, it is possible to selectively and appropriately identify the blood vessel or the like that is to be diagnosed with the aid of a contrast agent.

According to the magnetic resonance imaging apparatus of the present embodiment, it is possible to set and change the TI for each of the plurality of tag regions which are set in the same imaging sequence. Therefore, by setting a suitable TI in accordance with the velocity of blood flow that is to be visualized and the recovery time of the substantial longitudinal magnetization that is to be subjected to signal suppression by the IR pulse, it is possible to provide more appropriate non-contrast MRA.

According to the magnetic resonance imaging apparatus of the present embodiment, by using the TI setting assistance information, it is possible to observe a variety of actual MR images obtained under different TI setting values and to make quick determination on a suitable TI. Therefore, it is possible to provide best suitable visualization of the blood vessel and to thus eliminate the necessity of additional imaging due to inappropriate TI settings.

According to the magnetic resonance imaging apparatus of the present embodiment, when non-contrast MRA is performed using a plurality of tag regions, it is possible to generate a variety of differential images by difference computing processing based on a combination of ONs and OFFs of the spatial-selective pulses. Therefore, by appropriately combining the ONs and OFFs of the spatial-selective pulses to the tag regions of the MR image for use in the difference computing processing, it is possible to more appropriately visualize the blood vessel and the neighborhood that is to be diagnosed.

Second Embodiment

Next, a second embodiment of the present invention will be described. The magnetic resonance imaging apparatus 1 according to the present embodiment has a function (tag region setting assistance function) for assisting the settings of tag regions. The setting of a plurality of tag regions using this function is performed in step S3 of FIG. 10 and step S1 of FIG. 15, for example.

The setting of the plural tag regions according to the tag region setting assistance function is performed as follows. That is, an imaging range and a plurality of tag regions are set on a positioning image at a desired position and in desired size and shape via the input unit 13 or through intervention of a user interface GUI. Moreover, a flip angle (FA) and a TI are set for each of the tag regions, similarly, via the input unit 13 or through intervention of a user interface GUI. It is to be noted that an operator can arbitrarily change the setting procedures of the plural tag regions and the setting procedures of the flip angle and the TI for each of the tag regions.

Figure 16:
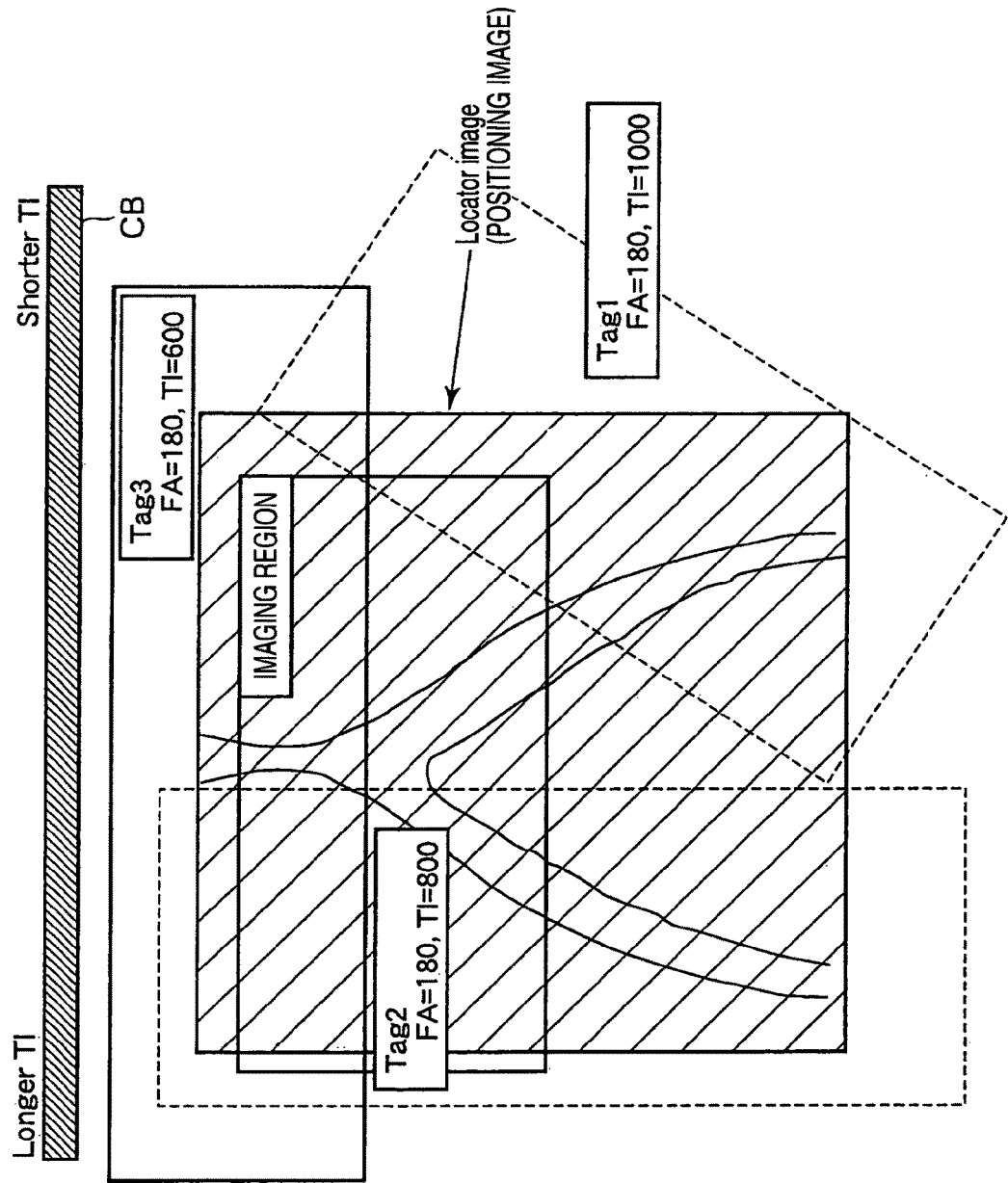
FIG. 16 is a diagram showing an example of a tag region setting assistance screen.

At the time of setting the position, TI, and the like of each of the tag regions, a tag region setting assistance screen as shown in FIG. 16 is displayed on the display unit 12. In this tag region setting assistance screen, the imaging range, the position, size, and shape of each of the tag region, on the positioning image, and the values of the flip angle and TI of the respective tag region are displayed. Moreover, the tag regions (outline thereof) are displayed with different colors depending on the length of TI and a color bar CB that indicates the length of TI is displayed. In the drawing, the respective tag regions are numbered as 1, 2, and 3 in the ascending order of TI. However, the numbering method is for the purpose of illustration only, and the tag region setting assistance function of the present embodiment is not limited to the illustrated tag region numbering method.

Figure 17:
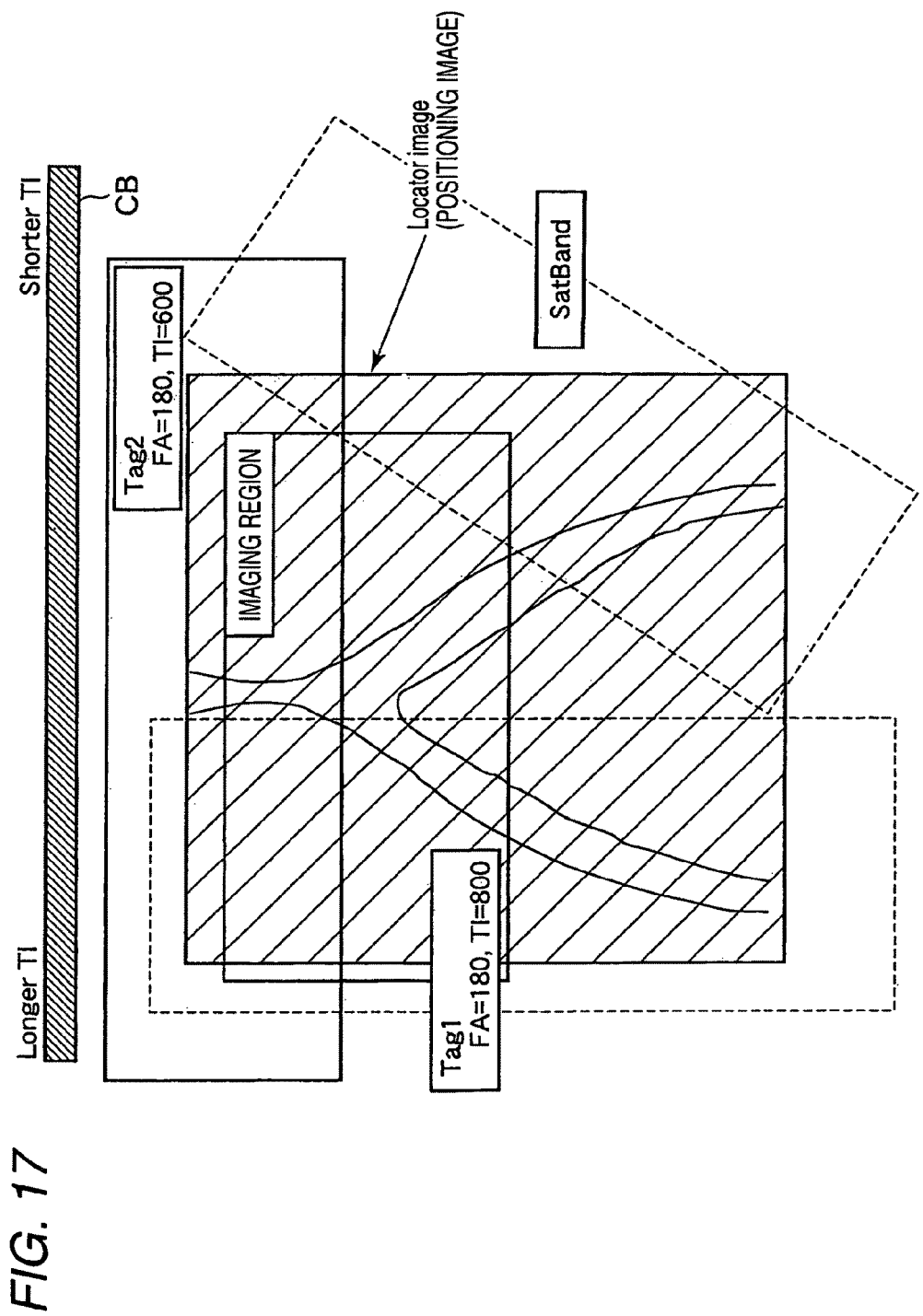
FIG. 17 is a diagram showing another example of the tag region setting assistance screen.

When the fat saturation pulses are applied in a spatial-selective manner, the regions (SatBand) to which the fat saturation pulses are to be applied may be set by the use of the tag region setting assistance function of the present embodiment. FIG. 17 is a diagram showing an example of the tag region setting assistance screen when the fat saturation pulses are applied in a spatial-selective manner. As shown in the drawing, the SatBand is set at a position on a positioning image displayed on the tag region setting assistance screen via the input unit 13 or through intervention of a user interface such GUI (in the example of FIG. 17, the SatBand is set at the upstream side of the imaging region and the respective tag regions).

According to the tag region setting assistance function described above, it is possible to set a plurality of tag regions and the SatBand at a desired position on the positioning image in an easy and quick manner. Therefore, an operator can observe the tag region setting assistance screen in which the positions of the imaging region, a plurality of tag regions, and the SatBand are set on the positioning image, to thereby visually recognize the relative positional relationship between the position, size, and shape of the respective tag regions, the imaging region and the SatBand in an easy and quick manner. Moreover, since the flip angle and the TI are displayed for each of the tag regions and the tag region is displayed in different colors depending on the length of TI, it is possible to visually recognize the length of the TI in each tag region and the difference in the length of the TI between tag regions in an easy and quick manner.

The present invention is not limited to the embodiments, but various modifications can be made to the components at the practicing stage without departing from the spirit of the invention. Specific examples of the modifications are as follows.

(1) The functions according to the embodiments may be realized by installing a program for executing the processes in a computer such as workstation and deploying the program in a memory. At this time, the program capable of causing the computer to execute the method may be distributed by being stored in a recording medium such as a magnetic disc (including a floppy (the registered trademark) disc and a hard disc), an optical disc (including CD-ROM and DVD), or a semiconductor memory.

(2) In the embodiments described above, description was made for the case of the breath synchronization method. However, the non-contrast MRA function of the present invention is not limited to the case where the breath synchronization is used. For example, when it is desired to perform imaging on the heart, an electrocardiographic synchronization method may be used in lieu of the breath synchronization method. Moreover, when imaging the head part, the legs and arms, or the like, the imaging can be performed using only the function of the non-contrast MRA without the breath synchronization method or the electrocardiographic synchronization method. Furthermore, the recovery time of the transversal or longitudinal magnetization in a target region may be calculated by a predetermined method and the apparatus per search engine may generate a pseudo trigger signal based on the calculated time.

(3) In the embodiments described above, the position of the tag regions, on the positioning image may be stored as diagnostic assistance information for later use. For example, in a monitor-based diagnosis for a patient as prognosis, the information on the position of the same tag region as the previous one may be useful in performing imaging that sets a tag region at the same position as the previous one in order to observe the post-surgery development. In such a case, by setting a present positioning image so as to correspond to the previous positioning image in which the position of the tag region is recorded, it is possible to automatically set the tag region at a position corresponding to the previous imaging.

(4) As is obvious from the embodiments, when more than one tag regions are set, the spatial-selective IR pulse and the non-selective IR pulse may be used together depending on necessity. Moreover, a portion of at least one tag region may not overlap with the imaging region (FOV) and may be located outside the imaging region, for example. In such a case, by using the spatial-selective IR pulse and the non-spatial-selective IR pulse together such that the non-spatial-selective IR pulse is applied to the entire regions of the imaging region including at least one tag region, and thereafter, the spatial-selective IR pulse is applied to the at least one tag region, it is possible to realize excellent non-contrast MRA.

Furthermore, a variety of other embodiments can be made by appropriately combining a plurality of components described in the exemplary embodiments. For example, several components may be omitted from the ensemble of components illustrated in the exemplary embodiments. In addition, components of different exemplary embodiments may be appropriately combined.

What is claimed is:

1. A magnetic resonance (MR) imaging apparatus comprising:
static and gradient magnetic field generators, at least one RF coil for transmitting and/or receiving RF signals to/from a patient when disposed within said magnetic field generators and at least one programmed computer system and associated memory connected to control the gradient magnetic field generators and RF transmitter and receiver circuits coupled to said at least one RF coil;
said at least one computer system being
configured (a) to accept an input individually designating at least one of position, shape and size for each of a plurality of tag regions, (b) to accept an input individually of a time period from an RF tag pulse to an imaging pulse for each of the plurality of tag regions, and (c) to respectively set the period for each of the plurality of tag regions, the plurality of tag regions being at least partially spatially located within an MR imaging region;
configured to apply the RF tag pulse to each tag region based on the respectively corresponding set period, apply the imaging pulse to the MR imaging region after applying the plurality of RF tag pulses to the plurality of tag regions, and acquire MR echo signals from the MR imaging region; and
configured to reconstruct an image of the MR imaging region based on said acquired MR echo signals,
wherein said acquired MR echo signals emanating from at least one of said MR tag regions are of different intensity compared to acquired MR echo signals emanating from elsewhere in said MR imaging region.

2. The magnetic resonance imaging apparatus according to claim 1, wherein the plurality of tag regions are all set within the imaging region.

3. The magnetic resonance imaging apparatus according to claim 1, wherein:
the at least one computer system is configured to accept an input preventing the plurality of tag regions from overlapping with each other.

4. The magnetic resonance imaging apparatus according to claim 1, wherein:
the at least one computer system is configured to accept an input causing at least portions of the plurality of tag regions to overlap with each other.

5. The magnetic resonance imaging apparatus according to claim 1, wherein:
the at least one computer system is configured to accept an input designating at least one of the plurality of tag regions to include another tag region.

6. The magnetic resonance imaging apparatus according to claim 1, further comprising:
said at least one computer system being configured to designate a tag pulse flip angle or time lapse from application of the tag pulse to start of image data acquisition for each of the plurality of tag regions.

7. The magnetic resonance imaging apparatus according to claim 1, wherein:
the at least one computer system is configured to apply a tag pulse to a first of the plurality of tag regions and subsequently to a second of the plurality of tag regions, and to acquire MR imaging data from the imaging region, after said tag pulses have been applied to said first and second tag regions, using a common MR imaging sequence.

8. The magnetic resonance imaging apparatus according to claim 1, wherein:
each tag pulse is an IR (inversion recovery) pulse applied together with a selective gradient magnetic field, and the image of the imaging region is a non-contrast MRA (magnetic resonance angiography) image.

9. The magnetic resonance imaging apparatus according to claim 1, further comprising:
said at least one computer system being configured to accept inputs that set the plurality of tag regions and respectively associated time lapses from tag pulse application to the start of MR imaging data acquisition for each of the plurality of tag regions using a previously obtained positioning image; and
said at least one computer system being coupled to a display and configured to display thereon information including respective positions of the tag regions relative to the positioning image and a respectively corresponding time lapse from application of the tag pulse to the start of imaging data acquisition for each of the tag regions.

10. The magnetic resonance imaging apparatus according to claim 1, wherein:
said memory is configured to store therein respective positions on the positioning image of the tag regions used in the acquisition of MR imaging data.

11. The magnetic resonance imaging apparatus according to claim 1,
wherein said at least one computer system is further configured to accept inputs setting information as to whether a tag pulse is to be applied or not for each of plural tag regions, and to acquire the imaging data based on information set for each of plural tag regions, as to whether a tag pulse is to be applied or not.

12. A magnetic resonance (MR) imaging method comprising:
accepting, individually designated for each of a plurality of tag regions, (a) at least one of the position, shape and size, (b) accepting an input individually of a period from an RF tag pulse an imaging pulse for each of the plurality of tag regions, and (c) to respectively set the time period for each of the plurality of tag regions, the plurality of tag regions being at least partially spatially located within an MR imaging region;

applying the RF tag pulse to each tag region based on the respectively corresponding set period, apply the imaging pulse to the MR imaging region after applying the plurality of RE tag pulses to the plurality of tag regions, and acquiring MR echo signals from the MR imaging region, and reconstructing an image of the MR imaging region based on MR echo signals acquired as the MR imaging data, said acquired MR echo signals emanating from at least one of said tag regions being of different intensity compared to acquired MR echo signals emanating from elsewhere in said MR imaging region.

13. A magnetic resonance (MR) imaging apparatus comprising:

static and gradient magnetic field generators, at least one RF coil for transmitting and/or receiving RF signals to/from a patient when disposed within said magnetic field generators and at least one programmed computer system and associated memory connected to control the gradient magnetic field generators and RF transmitter and receiver circuits coupled to said at least one RF coil;

said at least one computer system being configured (a) to accept an input individually designating at least one of position, shape and size for each of a plurality of tag regions, (b) to accept an input individually of a period from an RF tag pulse to an imaging pulse for each of the plurality of tag regions, and (c) to respectively set the time period for each of the plurality of tag regions, the plurality of tag regions being at least partially spatially located within an MR imaging region;

configured to apply the RF tag pulse to each tag region based on the respectively corresponding set period, apply the imaging pulse to an MR imaging region after applying the plurality of RF tag pulses to the plurality of tag regions, and to acquire MR echo signals from the MR imaging region, and configured to reconstruct an image of the MR imaging region based on said acquired MR echo signals, said acquired MR echo signals emanating from at least one of said tag regions being of different intensity compared to acquired MR echo signals emanating from elsewhere in said MR imaging region.

14. A magnetic resonance (MR) imaging method comprising:

(a) individually designating at least one of the position, shape and size of tag regions for each of a plurality of tag regions, (b) individually setting a time period from an RF tag pulse to an imaging pulse for each of the plurality of tag regions, and (c) to respectively set the period for each of the plurality of tag regions, the plurality of tag regions being at least partially spatially located within an MR imaging region;

applying the RE tag pulse to each tag region based on the respectively corresponding set period, apply the imaging pulse to the MR imaging region after applying the plurality of RF tag pulses to the plurality of tag regions, and acquiring MR echo signals from the MR imaging region; and reconstructing an image of the MR imaging region based on acquired echo signals, said acquired MR echo signals emanating from at least one of said tag regions being of different intensity compared to acquired MR echo signals emanating from elsewhere in said MR imaging region.

\* \* \* \* \*